United States Patent [19]

Spencer

[11] Patent Number: 4,828,107
[45] Date of Patent: May 9, 1989

[54] DISPOSABLE CONTAINER FOR SYRINGES

[76] Inventor: Treesa Spencer, 21882 Winnebago, El Toro, Calif. 92630

[21] Appl. No.: 224,292

[22] Filed: Jul. 25, 1988

[51] Int. Cl.$^4$ ............................ B65F 1/16; A61M 5/32
[52] U.S. Cl. .................................... 206/366; 206/63.5; 220/1 T
[58] Field of Search ....................... 206/366, 63.5, 438; 220/1 T

[56] References Cited

U.S. PATENT DOCUMENTS

| | | | |
|---|---|---|---|
| 1,238,010 | 8/1917 | Fisher | 220/1 T |
| 4,738,362 | 4/1988 | Burns et al. | 206/336 |
| 4,779,728 | 10/1988 | Hanifl et al. | 206/336 |

Primary Examiner—Allen M. Ostrager
Attorney, Agent, or Firm—Weissenberger & Peterson

[57] ABSTRACT

An in-room sharps container for hospital rooms and the like provides superior safety, versatility and economy by featuring a tapered, stackable body with a permanently hinged cover which is irreversibly interlockable with the body and which carries a semicylindrical dome covering the major portion of a pivotable semicylindrical dump tray. The dump tray can be permanently locked for disposal of the container by an over-center biased pin which locks the dump tray in the closed position. A stepped notch is provided in the cover above the tray for unscrewing and dumping blood collection needles without touching them. Hollow carrying handles protect personnel from contact with contaminants on the exterior of the container when it is being carried.

11 Claims, 5 Drawing Sheets

4,828,107

DISPOSABLE CONTAINER FOR SYRINGES

FIELD OF THE INVENTION

This invention relates to disposable containers for used syringes and the like, and more particularly to a container which provides a high degree of safety and versatility.

BACKGROUND OF THE INVENTION

Disposal of used syringes, blood collection needles, and other so-called "sharps" presents a number of problems. For example, disposal containers (commonly known as sharps boxes) must themselves be disposable to prevent handling of sharps after their original disposal; they must be inexpensively positionable on-site, i.e. in each patient room or other location where sharps are used; they must be easily shippable; it must not be easily possible to remove syringes therefrom once they have been disposed of; aerosolation (i.e. the excaping of disease-carrying particles into the air by evaporation during disposal) must be minimized; overfilling of the container must be prevented; a full container must be irreversably lockable; the irreversible full-container lock should not be accidentally actuable; the container should provide a way to unscrew blood collection needles from their holder and discarding of them without touching them; and the full container must be conveniently handleable without danger of contaminating the handler.

Various types of sharps boxes have been used in the past to accomplish some of these objectives, but none have been fully satisfactory in all of the above respects.

SUMMARY OF THE INVENTION

The present invention fulfills all of the above requirements in an economical manner by providing a sharps box which has the following features:

(1) the boxes of this invention are nestable for shipment yet are shaped to securely stand alone, and have a permanently attached cover which cannot get separated from the box;

(2) once the cover is closed, it interlocks with the box body by an inaccessible interlock and cannot be reopened;

(3) the dump tray is a half-cylinder rotatable about its axis to assure positive parallel dumping of all sharps, and to impede rotation to the receiving position when the box is full;

(4) the dump tray is permanently covered against aerosolation except for a relatively small opening for the introduction of syringes and the like;

(5) a needle-engaging slot or notch is provided in the cover dome above the dump tray to hold a blood-collecting needle while it is being unscrewed from its holder, and then let the needle drop into the dump tray without being touched;

(6) a locking pin with an over-center resilient biasing arrangement is provided in a location not normally accessed in use, to permanently lock the dump tray in the fully closed position when the box is full; and (7) handles are provided on the ends of the box to form supports engageable with a wall rack for releasably mounting the box on a wall, and to allow personnel to carry the full box away from their body and with their hands out of the path of any possible leakage contamination of the outside of the box.

It is thus the object of the invention to provide a sharps box which features a high degree of safety yet is cost-effective.

DESCRIPTION OF THE PREFERRED EMBODIMENT

Figure 1:
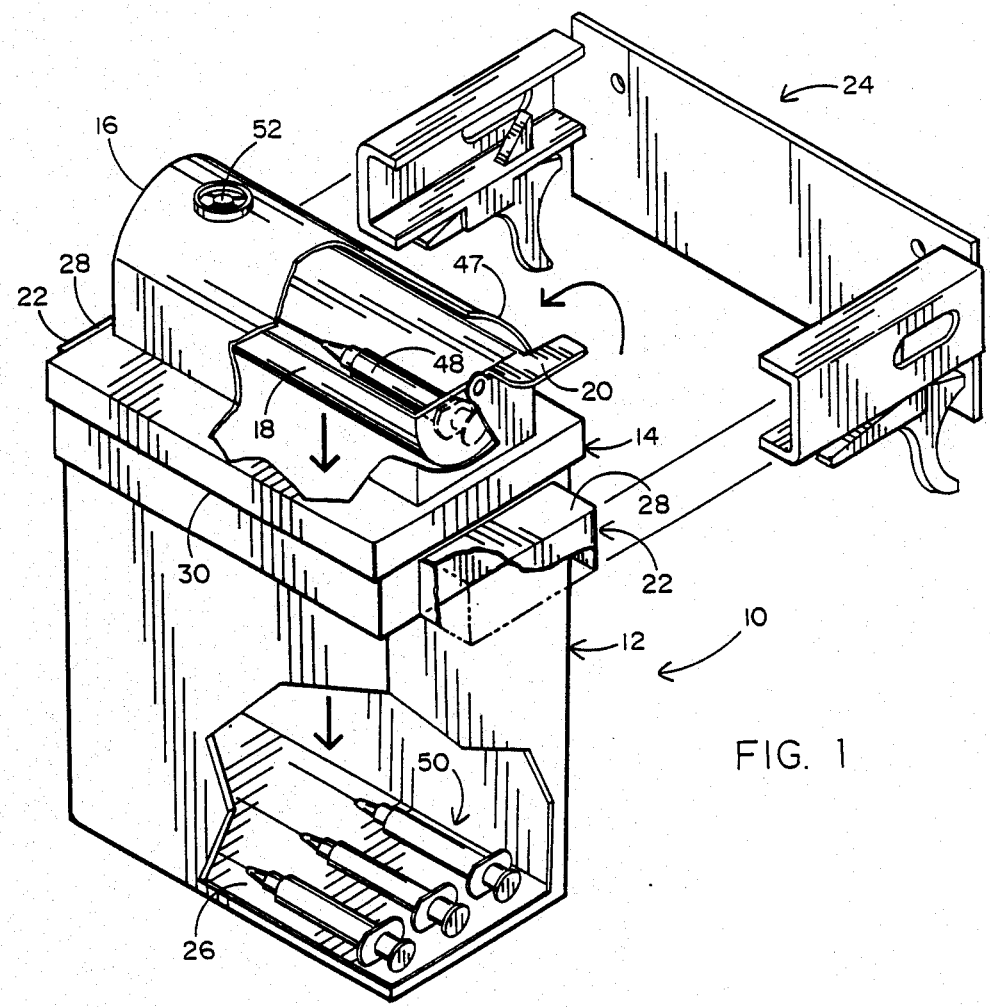
FIG. 1 is a perspective view, partially cut away, of the sharps box of this invention.

FIG. 1 shows the overall structure of the sharps box or container 10 of this invention. The container 10 includes a body 12 of a material resistant to penetration by the sharp objects to be disposed of, and a cover 14 of a similar material. The cover 14 includes a dome 16 within which a semicylindrical dump tray 18 is arranged for pivoting movement about its axis. The dump tray 18 is pivoted by means of a dumping lever 20. The operation of the dump tray 18 and its interaction with the dome 16 will be described in more detail hereafter.

On each of its ends, the container 10 is provided with hollow handles 22 which, in one use of the invention, may slide into an appropriate locking bracket generally indicated at 24 for releasable wall mounting of the container 10. Alternatively, the container 10 may rest on any flat surface on its flat bottom 26, which is made sufficiently wide and level to assure its remaining upright when jostled.

The hollow configuration of the handles 22 is an important safety factor in the handling of the container 10 after it is filled. The position of the handles at the ends of the container makes it possible to carry the filled container at either end as remotely from the body as possible, and the presence of the top plate 28 protects the carrier's fingers from any fluids which may have leaked from between the cover 14 and the body 12 if the filled container 10 had temporarily been placed on its side. In addition, the presence of the handles 22 makes it possible to avoid grasping the container 10 by its sides, which could accidentally be penetrated by the needles of syringes wedged transversely in the container 10 (although the material of the container 10 and its functioning as described hereinafter are designed to prevent this).

Figure 6:
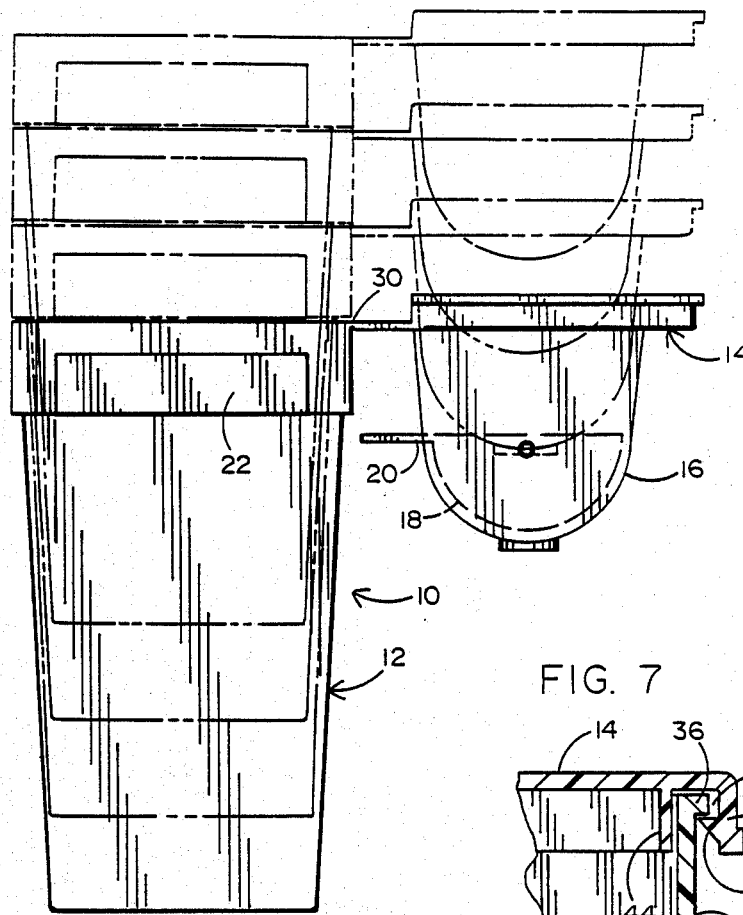
FIG. 6 is a schematic end elevation of a stack of nested boxes.

The body 12 of the container 10 of this invention is tapered downwardly so that a stack of containers 10 can be nested for ease of shipment and storage as shown in FIG. 6. The nesting of the bodies 12 is conventional; however, in prior art constructions, the container bodies and the container covers had to be packaged separately and then individually assembled at the destination. The container 10 avoids this inconvenience through the permanent attachment of cover 14 to body 12 by a living hinge 30. The dome 16 and the ends of dump tray 18 are also tapered, so that open covers 14 fit into each other in shipment as the bodies 12 do. When the containers 10 are unpacked, it is merely necessary to close the cover 14, and the container 10 is ready for use.

Figure 7:
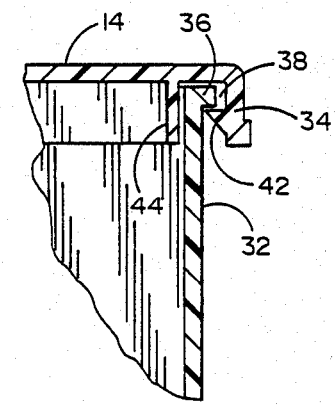
FIG. 7 is a detail cross section of the box of FIG. 1 showing the cover interlock.

It is important in the medical field to make it difficult to unauthorized persons to surreptitiously remove used syringes from the container 10 for illegal purposes. For this reason, the upper end of body wall 32 (FIG. 7) and the outer flange 34 of cover 14 are provided with a hidden interlock consisting of a square ridge 36 in the wall 32 and a matching recess 38 on the inside surface of the outer flange 34 of cover 14. The tapered surface 42 causes the flange 34 to resiliently bend outwardly as the cover 14 is being closed, and to snap into engagement with the wall 32 when the closing is complete.

An inner flange 44 on cover 14 prevents the wall 32 from being pushed inwardly to disengage the ridge 36 from the recess 38, while the outer flange 34 is made long enough to hide the nature of the cover-wall interlock from view.

Figure 2:
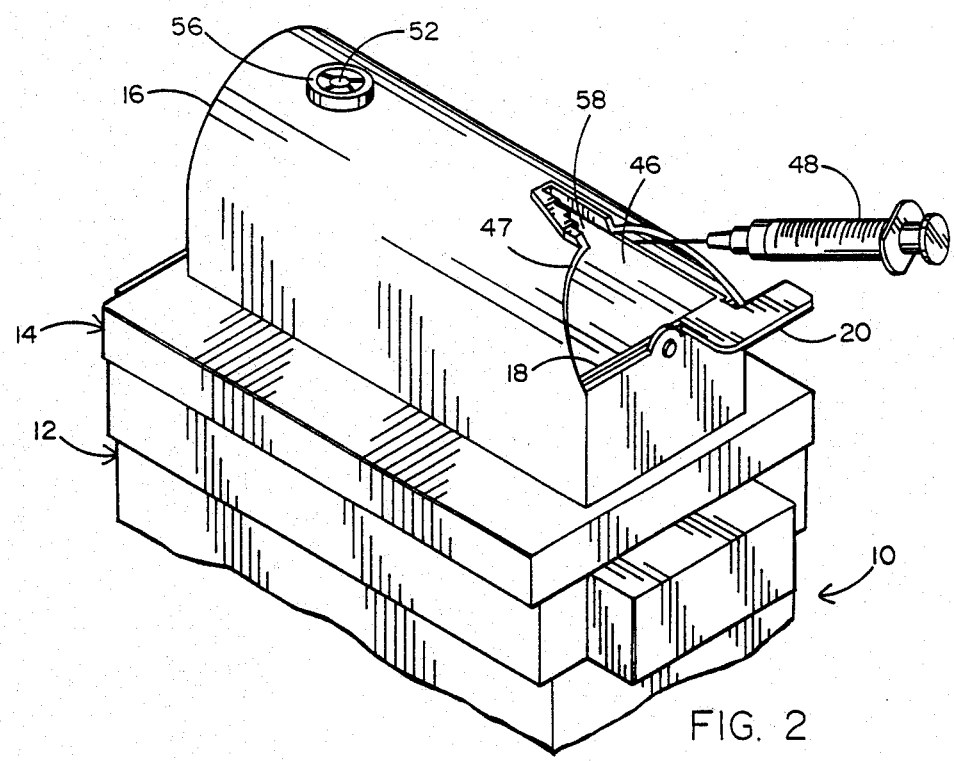
FIG. 2 is a detail view of the upper portion of the box of FIG. 1 showing the dump tray in the open position.
Figure 3:
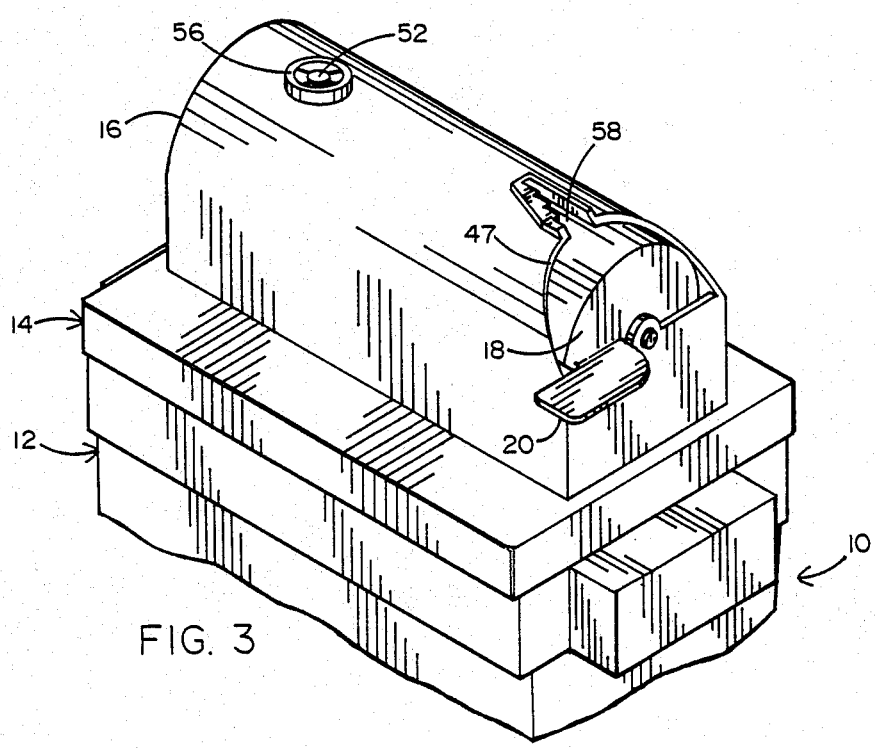
FIG. 3 is a view similar to FIG. 2 but showing the dump tray in the closed position.

As best shown in FIGS. 2 and 3, the dump tray 18 is operated by dumping lever 20 through which the dumping tray 18 can be pivoted about its axis between the open or receiving position of FIG. 2 and the closed or dumping position of FIG. 3. The dome 16 covers most of the dumping tray 18 when it is open to minimize aerosolation of any contaminants in the tray, but leaves an angled receiving opening 46, defined by the inclined edge 47 of dome 16, through which syringes and the like can be introduced into the dumping tray 18.

The location of the receiving opening 46 at the end of container 10, and the symmetry of container 10 about a longitudinal vertical plane through its center, make it possible to mount the container 10 in the bracket 24 for access from either the right or the left, or to position it with the opening 42 facing the operator on a low or narrow shelf.

The orientation of the receiving opening 46 is conducive to urging the user to deposit elongated objects such as a syringe 48 into the dumping tray in a generally horizontal position. When this is done, the syringe 48 will readily slide on the hard, smooth inner surface of tray 18 and roll into a fully horizontal position (FIG. 1) in the bottom of the semicylindrical dumping tray 18. The subsequent closure of dumping tray 18 will cause the syringe 18 to fall into the body 12 in parallel alignment with previously dumped syringes 50 for optimum safety and utilization of the space within body 12.

The semicylindrical configuration of the dumping tray 18 can also provide a signal that the container 10 is full by imposing a senseable resistance to, or even preventing, its rotation to the open position when discarded sharps are in the way of the edge of tray 18 as it rotates.

It will be noted that the semicylindrical shape of the dump tray 18 closes off the interior of the body 12 in both the open and the closed position. Consequently, nothing can fall out of the container 10 if it is accidentally inverted, as by falling off a table, in either position of the dump tray 18.

The dimensions of the opening 46 and of the dumping tray 18 are such that it is not possible to insert a hand into the body 12 to remove a used syringe therefrom unless the container 10 is nearly full, and difficult even then. Actually, syringe removal prevention does not become a significant problem until a container is removed from its patient room location and is left temporarily unattended in a disposal location. At that time, access to the interior of container 10 without aggressive destruction is totally prevented by the mechanism shown in FIGS. 4 and 5.

Figure 4:
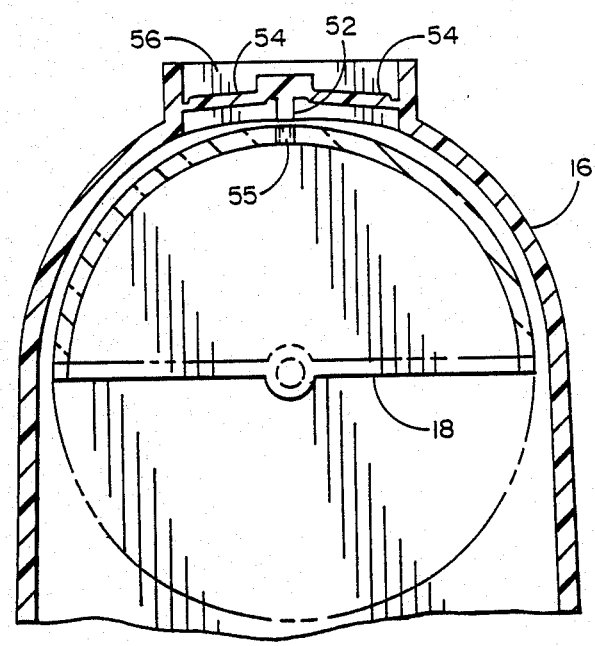
FIG. 4 is a cross section of the dome of the box cover showing the locking button disengaged.
Figure 5:
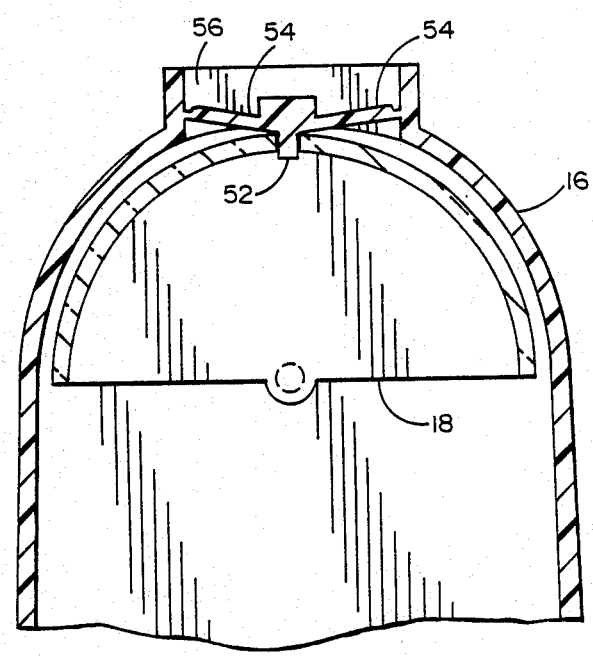
FIG. 5 is a cross section similar to FIG. 4 but showing the locking button engaged.

FIG. 4 shows the locking pin 52 in its unlocked position. In this position, the pin 52 is held clear of the dump tray 18 by spring flaps 54 which are preferably formed integrally with dome 16 and with the head of pin 52. When the box 10 is ready for removal and disposal, the head of pin 52 is depressed after the last dumping operation. This causes the over-center spring flaps 54 to snap into the position of FIG. 5, in which the pin 52 engages an aperture 55 in the closed dump tray 18 and permanently prevents it from being reopened.

The location of the locking pin 52 remote from the dumping lever 22 and its position in the wall 56 greatly reduces the chances of its being accidentally (thoughtlessly or ignorantly) engaged, as is the case with some prior art permanent closure devices. At the same time, the over-center spring flaps 54 cannot be pulled back up by hand.

Figure 8:
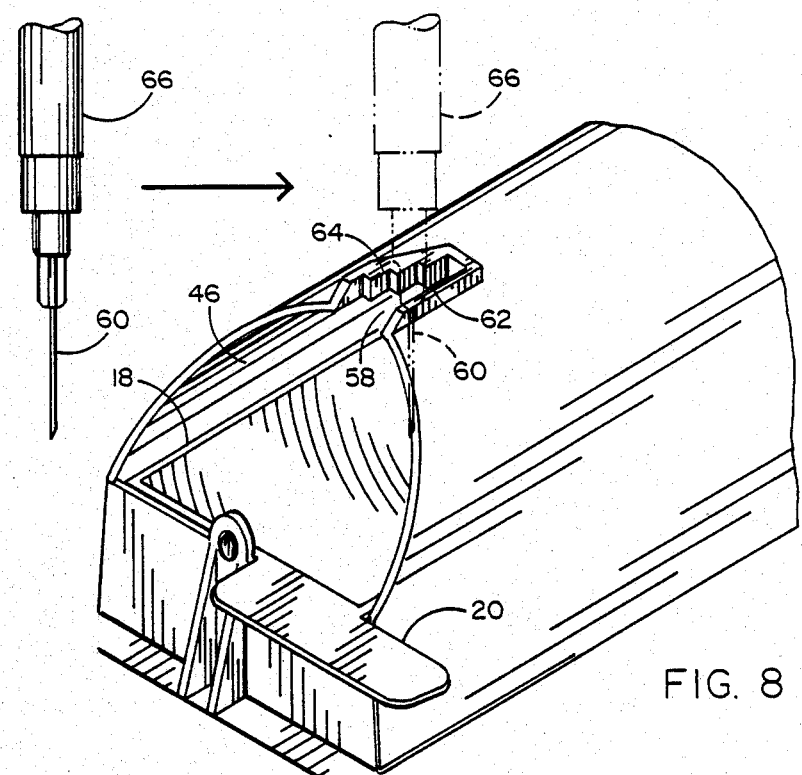
FIG. 8 is a detail perspective view illustrating the operation of the collection needle removal notch.
Figure 9:
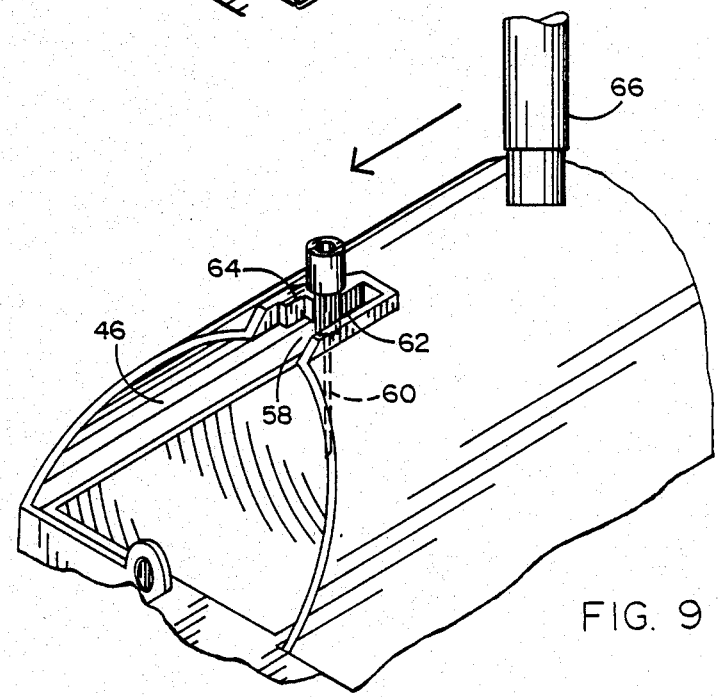
FIG. 9 is a view similar to FIG. 8 illustrating the nontactile disposal of the collecting needle.

FIGS. 8 and 9 illustrate the operation and purpose of the collection needle removal notch 58. Blood collection needles are normally unscrewed from their holder at the collection site and disposed of separately. For this purpose, the notch 58 in the dome 16 receives the shank of needle 60. That shank is normally flattened on two sides so as to be engageable by the common surface 62 and one of the stepped surfaces 64, depending upon the size of the needle 60. With the needle 60 in the notch 58 and thus over the open dump tray 18 (the notch 58 is blocked when the dump tray 18 is closed), the holder 66 can be unscrewed and then used to push the shank of the needle 60 out of notch 58 so that it falls into the dump tray 18, where it assumes a horizontal position for aligned disposal as previously described. This feature makes it possible to dispose of blood collection needles without touching them at all.

What is claimed is:

1. A disposal container for medical sharps comprising:
   (a) a puncture-resistant body for receiving discarded sharps; and
   (b) a cover for covering said body; said cover including:
      (i) a substantially semicylindrical dome;
      (ii) a substantially semicylindrical dump tray substantially coaxial with said dome and pivotable about said common axis between an open and a closed position;
      (iii) said dome being axially substantially coextensive with said dump tray but having an inclined edge forming a receiving opening giving access to the interior of said dump tray when said dump tray is in said open position.

2. The container of claim 1, in which said cover further includes a dumping lever on said dump tray for rotating said dump tray between said open and closed positions.

3. The container of claim 1, in which the walls of said body and an end wall of each of said dome and dump tray are tapered, and said cover is hingedly attached to said body.

4. The container of claim 3, in which said cover includes a pair of depending flanges on a side thereof spaced from said hinge, said flanges being disposed so as to receive the upper end of a wall of said body therebetween when said cover is closed, said body wall and one of said flanges having mating interlocking ridge and recess means for non-releasably interlocking said cover and body when said cover is closed.

5. The container of claim 4, in which the outer of said flanges is of sufficient extent to prevent visual observation of said ridge and recess means when said cover is closed, and the inner of said flanges is sufficiently close to said wall to prevent said ridge and recess means from being pushed out of engagement with one another when said cover is closed.

6. The container of claim 1, in which said body has a handle formed thereon substantially adjacent the interface between said body and said cover, the portion of said handle which is engaged by the fingers when said container is carried being open downwardly but being closed on both sides and the top to protect said fingers from contact with fluid leakage at said interface.

7. The container of claim 5, in which said container is symmetrical about a vertical plane through its center.

8. The container of claim 1, in which said dump tray has an aperture formed therein, said container further comprising:

(c) pin means for selectively engaging said aperture to lock said dump tray in the closed position;
(d) over-center biasing means for normally holding said pin means in an non-engaged position but maintaining said pin means in the engaged position once said pin means has been pushed toward said dump tray when said dump tray is closed.

9. The container of claim 8, in which said dump tray includes a dumping lever for actuating said dump tray, and said pin means is positioned on said dome in a location remote from said receiving opening and said dumping lever.

10. The container of claim 1, in which said cover further includes (iv) a notch formed in said inclined edge above said dump tray;
(v) said notch being shaped to engage the shank of a blood collection needle rotatably detachable from a holder, and to retain the same against rotation when said holder is rotated to detach said needle therefrom.

11. The container of claim 10, in which a side of said notch is stepped to provide successive shank-engaging areas parallel to the opposite side of said notch but at different distances therefrom.

* * * * *